United States Patent [19]

Downes

[11] Patent Number: 5,413,553
[45] Date of Patent: May 9, 1995

[54] REMEDIAL PROPHYLAXIS FOR CARPAL TUNNEL SYNDROME

[76] Inventor: John W. Downes, 1816A Ashborough Rd., Marietta, Ga. 30067

[21] Appl. No.: 66,333

[22] Filed: May 21, 1993

Related U.S. Application Data

[63] Continuation of Ser. No. 978,875, Nov. 19, 1992, abandoned.

[51] Int. Cl.$^6$ .................... A61F 5/00; A41D 19/00
[52] U.S. Cl. .................... 602/21; 602/64; 2/159
[58] Field of Search .......... 602/5, 6, 21, 62–64; 482/44; 2/16, 20, 158, 159, 161.1, 162, 161.6, 161.7; 273/54 B, 166; 128/879

[56] References Cited

U.S. PATENT DOCUMENTS

| | | | |
|---|---|---|---|
| 1,362,461 | 12/1920 | Anast | 128/879 X |
| 1,471,948 | 10/1923 | Cox et al. | 602/21 X |
| 2,141,739 | 12/1938 | Burke | 2/158 |
| 2,369,210 | 2/1945 | Capossela | 2/16 |
| 2,388,330 | 11/1945 | Jungmann | 2/16 |
| 3,152,337 | 10/1964 | Barry | 273/54 B |
| 3,327,703 | 6/1967 | Gamin | 602/21 |
| 3,394,408 | 7/1968 | Bush | 273/166 |
| 3,533,407 | 10/1970 | Smith | 602/64 |
| 3,788,307 | 1/1974 | Kistner | 602/21 |
| 4,309,991 | 1/1982 | DeMarco | 602/64 |
| 4,374,439 | 2/1983 | Norman | 273/54 B X |
| 4,386,775 | 6/1983 | Kouros | 273/54 B |
| 4,531,241 | 7/1985 | Berger | 2/20 X |
| 4,552,359 | 11/1985 | McDonald | 273/54 B |
| 4,561,122 | 12/1985 | Stanley et al. | 2/20 |
| 4,565,195 | 1/1986 | Eisenberg | 128/879 |
| 4,658,441 | 4/1987 | Smith | 2/20 X |
| 4,709,694 | 12/1987 | O'Connell | 602/21 |
| 4,732,142 | 3/1988 | Harlburt et al. | 602/21 X |
| 4,850,341 | 7/1989 | Fabry et al. | 602/21 X |
| 4,873,998 | 10/1989 | Joyner | 128/879 |
| 4,894,866 | 1/1990 | Walker | 2/20 X |
| 4,953,568 | 9/1990 | Theisler | 128/879 X |
| 4,966,137 | 10/1990 | Davini | 602/21 |
| 5,058,573 | 10/1991 | Hess et al. | 602/21 |

Primary Examiner—Linda C. M. Dvorak
Attorney, Agent, or Firm—Louis T. Isaf; Jeffrey R. Kuester

[57] ABSTRACT

A remedial prophylaxis for carpal tunnel syndrome to provide for the decompression of the structures of the carpal tunnel by using a glove having finger holes for the fourth finger and thumb and a tensioning strap for circumscribing the palmar and dorsal regions of the hand to hold the first and fifth metacarpal regions of the hand in fixed opposition to each other to effect a reducing of the stretch of the transverse carpal ligament and the deepening of the carpal tunnel for relieving the compression force on the median nerve without reducing the manual dexterity of the hand.

12 Claims, 4 Drawing Sheets

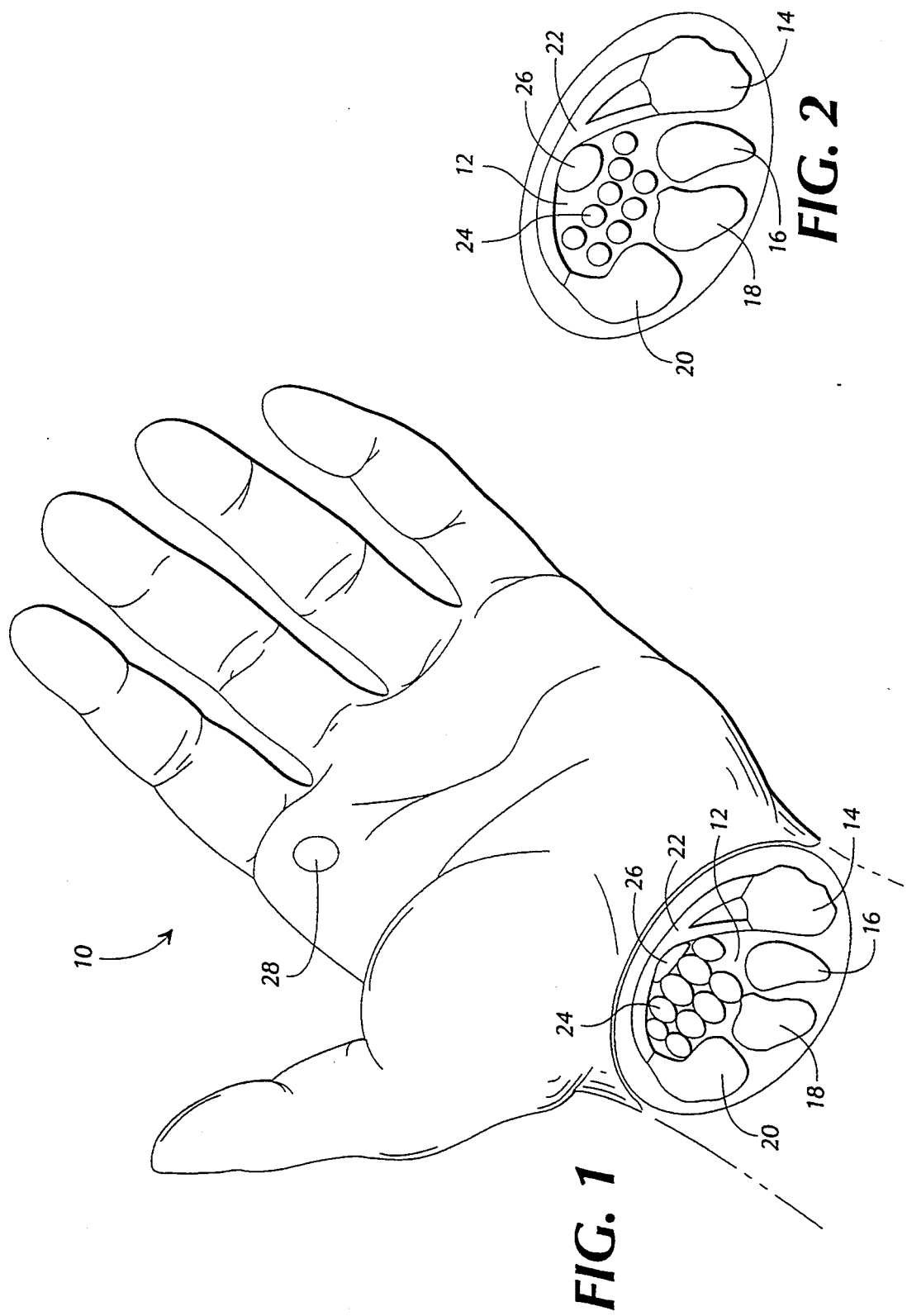

REMEDIAL PROPHYLAXIS FOR CARPAL TUNNEL SYNDROME

CROSS-REFERENCE TO RELATED APPLICATION

This application is a continuation of U.S. patent application Ser. No. 07/978,875, filed Nov. 19, 1992, now abandoned.

BACKGROUND OF THE INVENTION

When G. S. Phalen introduced a contemporary investigation of "Spontaneous Compression of the Median Nerve of the Wrist" at the 99th annual meeting of the American Medical Association few people considered the matter of great importance. Today the "spontaneous compression" is recognized as Carpal Tunnel Syndrome and has become the most prevalent cumulative trauma disorder reported in the workplace. The proliferation of articles has made carpal tunnel syndrome a household word creating increased public concern but there remain only a few options for treatment.

The exact mechanical basis for carpal tunnel syndrome varies among authors, but the basic premise is consistent. The carpal tunnel is a relatively fixed structure through which several tendons and the median nerve, the main nerve for the fingers, travel. When swelling or inflammation of the tissues occurs the median nerve is pinched creating the signs and symptoms of carpal tunnel syndrome.

Symptoms are believed to be caused by factors which increase the size of the tissues within the carpal tunnel, an abnormal condition which narrows the tunnel, or posterior sympathetic cervical stress syndrome. The latter syndrome is characterized by irritation of the lower four cervical nerve roots, which contain preganglionic sympathetic fibers. In this condition, however, pain is usually exhibited in the entire hand instead of only in the median nerve distribution.

Prior to the onset of acute symptoms muscle weakness or paresthesia is often experienced. Patients will often complain of cutaneous sensory irritation characterized by numbness, burning, or tingling in the first three fingers and the radial half of the ring finger, but usually not the fifth digit. When the patient says that his or her hand feels numb, it usually indicates motor impairment, not sensory. In addition, there can be impairment in the ability to sense heat and cold, fine tactile discrimination, and pain, since the median nerve carries most of the sympathetic nerve supply to the hand.

The pain can occur during daily activities, nocturnally, or upon awakening. Nocturnal pain in the median nerve distribution of the hand is considered to be pathognomonic for carpal tunnel syndrome. This pain can usually be relieved by shaking or rubbing the hand or arm or immersing the affected limb in warm water. The acute attack usually subsides within a few minutes to an hour.

Referred pain has been documented to radiate up into the forearm, elbow, and shoulder, thus mimicking a myriad of other syndromes. The patient may also complain of motor involvement characterized by difficulty in holding a pencil, opening a jar or dropping objects for no apparent reason. The contribution of occupational factors is often overlooked, despite recent research indicating that up to 47% of all cases of carpal tunnel syndrome may be caused by workplace factors.

The carpal tunnel is an osseofibrous structure formed by the flexor retinaculum and the anterior surfaces of the proximal and distal rows of the carpal bones. From medial to lateral the proximal bones are pisiform, triquetrum, lunate and scaphoid. From medial to lateral the distal bones are hamate, capitate, trapezoid and trapezium. The flexor retinaculum is also known as the transverse carpal ligament, the annular ligament, the anterior annular ligament or the deep transverse carpal ligament. The flexor retinaculum is the size of a "postage stamp" with two surfaces and four borders.

The landmark for the proximal border of the flexor retinaculum is the distal crease at the wrist. The anterior surface of the flexor retinaculum is the origin of the thenar and hypothenar muscle groups responsible for the opposition of digits and pinch strength. The dorsal surface of the flexor retinaculum is associated with the contents of the carpal tunnel containing:

1) nine tendons (4 superficial, 4 deep, 1 pollicis longus)
2) one median nerve
3) two bursae (ulnar and radial)

The median nerve lies in front of the bursae of the flexor tendons and close to the dorsal surface of the flexor retinaculum. The function of the flexor retinaculum is to retain the long flexor tendons close to the skeleton so that the tendons do not spring away from each joint as it is flexed. The fibrous retinaculum increases the strength of the carpus and the efficiency of the muscles. The actual borders of the flexor retinaculum traverse from the medial (hypothenar) attachment on the pisiform and hamulus of the hamate to the lateral (thenar) attachment at the tubercle of the navicular (scaphoid) and the tubercular ridge of the greater multangular (trapezium).

The current protocol for conservative treatment focuses on splinting. The basis for this approach comes from findings that patients exhibiting carpal tunnel syndrome had elevated resting intracanal pressure. Wrist flexion and extension studies have demonstrated that the intracanal pressure increases from three to six times that found in the neutral position. Extension resulted in somewhat greater increases than flexion, especially in the distal aspect of the tunnel. Immobilizing the wrist in a neutral position is the popular treatment. Steroid injection is the drug therapy of choice but, due to the potential danger of chemical neuritis or aseptic necrosis, its value is limited to three or four administrations.

The final step in treating carpal tunnel syndrome has been decompression of the carpal tunnel by transecting the flexor retincaculum. A number of authorities indicate the long term effects do not substantiate the decompression theory. Despite its high incidence and its reputation for simplicity and efficiency, carpal tunnel release does not invariably produce good results, and dissatisfied patients are not infrequently encountered. Unsatisfactory results are caused by inaccurate diagnosis and all too frequently, iatrogenic surgical complications. The *Journal of the American Medical Association* reports that the initial relief provided by carpal tunnel surgery may be shadowed by significant scar pain and weakness in almost a third of the subjects after two years. The surgery, in which the carpal tunnel is decompressed by release of the transverse ligament and debridement, is the most common surgery in the workers' compensation population.

The published results of neutral splinting cites 67% of the subjects reporting symptom relief after splint use.

One of the problems with this protocol is the bulky bracing which produces gross restriction at the radiocarpal joint which is proximal to the actual carpal tunnel. Significantly higher success rates were reported by using lightweight functional design splints which could be worn full time and which minimally restrict function. Various types of splinting, bracing, shock absorbing, and padding are disclosed in the patent references discussed below.

U.S. Pat. No. 4,883,073 (Aziz) discloses a wrist splint with integral elements for reducing aggravation of the median nerve by maintaining the wrist in a neutral unflexed position. The wrist movement is considerably restricted. U.S. Pat. No. 5,014,689 (Meunchen, et al.) describes a brace for the hand that limits hand extension and flexion as well as ulnar and radial deviation. U.S. Pat. No. 4,899,763 (Sebastian, et al.) describes a therapeutic appliance for the wrist and lower forearm having inflatable chambers and an elastic loop or strap wrapped around the thumb for immobilizing the wrist and acting as a means for preventing injury to the neural, tendinous and ligamentous tissues. These three devices are designed specifically to restrict the motion of the hand and wrist, and as such would have little value or utility to an individual who must return to the workplace or desires to pursue normal daily routines.

Another group of patent references describes gloves or other related devices that shield the section of the hand and/or wrist where median nerve exposure is greatest. These devices protect against impact by cushioning, but do not act to relieve median nerve pressure nor the pain from carpal tunnel syndrome. U.S. Pat. No. 5,031,640 (Spitzer) describes a contoured pad for tool handles and the like such that the median nerve is protected during the gripping process. U.S. Pat. No. 4,905,321 (Walunga) describes a sports glove that combines hand protection and an attached wrist strap for supporting wrist tendons during lifting of heavy weights. U.S. Pat. No. 4,561,122 (Stanley, et al.) discloses a glove with shock absorbing padding designed to maintain a palmar/dorsal balance of sensation to retain cognizance by touch for baseball players.

U.S. Pat. No. 4,958,384 (McCrane) describes a safety glove with a stiffening rib built into the back or non-palmar side, and an elastic strip that can be wrapped around the wrist area more than one time in an attempt to prevent hyperextension in sports or work activities. U.S. Pat. No. 4,850,341 (Fabry, et al.) describes a glove for inhibiting carpal tunnel syndrome pain by using a pad to protect the median nerve from vibration and shock. U.S. Pat. No. 4,531,241 (Berger) describes a glove for use in protecting hands from impact machinery (jack hammer, rivet guns, etc.) with a cushioning pad on both the outside and inside of the palmar side is used with the pads extending down and over the wrist.

In certain cases thumb injuries can be associated with carpal tunnel syndrome and the following patent references are concerned with protection or immobilizing the thumbs, but do not address the carpal tunnel syndrome problem. U.S. Pat. No. 4,565,195 (Eisenberg) describes a glove with a retainer to restrict the motion of the thumb if it is bent abnormally. U.S. Pat. No. 4,658,441 (Smith) describes a one piece thumb support that covers the thumb/index finger. web. U.S. Pat. No. 4,935,568 (Theisler) describes a flexible, adjustable thumb brace that restricts the motions of the thumb and is specific to protecting an injured thumb.

None of the foregoing patents addresses relief of pressure on the median nerve or protection/alleviation of the pain from carpal tunnel syndrome. However, one patent reference does suggest the use of compressive forces over the wrist area of the forearm to relieve carpal tunnel stress.

U.S. Pat. No. 4,966,137 (Davini) discloses the use of a semi-rigid plastic clamp with open ends that is molded in place over a patient's wrist. The open ends of the clamp are curved inwardly, and are placed over the location of the median nerve in the wrist. An overwrap elastic bandage is used to pull the clamp ends together and produce compressive forces on the radius and ulna bones which, in turn produces a decompression effect on the median nerve and claims some expansion of the carpal tunnel. The limitations of this device are: (a) position of application is proximal to the anatomical structures comprising carpal tunnel and only a minor carpal tunnel enlargement can be achieved without causing patient discomfort and skin trauma; (b) removal, adjustment, and replacement must be carried out by a medical professional; and (c) non-porosity and bulk of the device will likely exacerbate contact dermatritis or dermative sensitivity. As in the cases of the patent references discussed above, this reference does not address alleviation of pain or remedial effects for carpal tunnel syndrome accomplished by the present invention through the use of compressive inwardly directed force over the metacarpal-phalangal region as more fully described below.

As surgical intervention should be the last choice in treatment for any condition, including carpal tunnel syndrome, the usual regimen utilizes various types of braces, splints and medications. Although functional, these devices are often bulky and uncomfortable. Further, their utility resides in limiting the degree of motion of a patient's hand and wrist to alleviate median nerve pain and additional irritation. These motion restrictions prevent a patient from returning to the workplace in a fully productive condition as well as significantly inhibiting the performance of normal daily personal routines.

It is not unreasonable to state that these splints and braces require a change in life style for a person afflicted with carpal tunnel syndrome. The importance of the above factors is highlighted by the fact that the Occupational Safety and Health Agency, a federal regulatory agency, no longer permits workers to return to their jobs if splints are used in the treating of carpal tunnel syndrome. The corresponding loss of productivity plus insurance and other related health care costs represent significant economic burdens on both workers and industries.

The present invention, hereinafter sometimes referred to as the Carpal Tunnel Mitt or CTM, obviates the limitations described above, and provides a unique new approach to the conservative treatment of carpal tunnel syndrome. A review of the technical literature, commercially available products, and patent references have not disclosed the use of any similar designs or utility. The Carpal Tunnel Mitt has taken the optimal aspects of functional anatomy and blended the desire for a lightweight functional splint that can be worn full time. The mechanism that makes the Carpal Tunnel Mitt unique is approximating the borders of the flexor retinaculum without muscle contraction and inhibiting only the very end stages of wrist flexion and extension to reduce the stressors at the carpal tunnel. The mechanical opposition of the 1st to the 5th metacarpal-phalangal region deepens the carpal tunnel allowing for natural decompression forces on the structures within the carpal tunnel. It also provides maximum space at the distal aspect of the carpal tunnel where the highest incidence of impaired sensory conduction of the median nerve is seen. This is distal to any actual flexion-extension mechanics which occur at the radio-carpal and mid-carpal region.

Application of the Carpal Tunnel Mitt is corrective, rehabilitative and preventative spanning all occupations where repetitive strain injuries exist. The CTM provides relief in acute and chronic cases and may become essential in management of the Double Crush Syndrome. Some carpal tunnel symptoms have been attributed to cervical nerve root compression when seen during waking hours versus nocturnal onset. This expanded view of cervical interaction is best managed through Chiropractic care or practitioners of manual medicine in conjunction with application of the Carpal Tunnel Mitt which will provide the maximum opportunity for conservative management and relief of the signs and symptoms of carpal tunnel syndrome, thus reducing the need for drug therapy and surgery.

It is, therefore, an object of the present invention to provide a means for non-invasive relief from the pains associated with carpal tunnel syndrome having only minimal restrictions of hand and wrist motions.

A further object of the invention is to provide a lightweight flexible apparatus made of porous, stretchable fabric that allows the skin to breathe while it is being worn.

Another object of the invention is to provide a means for orienting a tensioning device to retain the bones and associated ligaments of the carpal tunnel in a fixed position while the invention is in place and thereby relieve the pressure on the median nerve during various manual activities.

A still further object of this invention is the enlargement of the dimensions of the carpal tunnel by the application of natural decompression forces effectuated by the mechanical deepening of the carpal tunnel by allowing the flexor retinaculum to contract by holding the proximal bones of the hand in a fixed spaced relationship.

Relief of the pressure on the median nerve and other components of the carpal tunnel and subsequent self-healing are directly related to the degree of the carpal tunnel enlargement. The decompression is effected by the displacement of the tendons, bursae and median nerve which return to their normal location when decompression is terminated.

An additional object of the present invention is that it can be used advantageously in combinations with or attached to splints of various types for those treatments in which it is medically necessary to support and/or immobilize the wrist and/or forearm area.

For example the CTM can be used in conjunction with the Sebastian therapeutic appliance or the Aziz remedial device. These examples are illustrative and should not be considered as a limitation. Additionally, the CTM could be consolidated with various safety or sports glove designs; for example with Stanley, et al. and McCrane, or any of the currently available commercial gloves. Again, these examples are illustrative and should not be considered as a limitation on the scope of the invention.

Other objects will appear hereinafter.

SUMMARY OF THE INVENTION

The present invention is a remedial prophylaxis for carpal tunnel syndrome comprising a lightweight glove-like mitt for placing over the hand which can be worn for extended periods of time and which holds firmly the first and fifth metacarpal phalangeal regions in opposition or approximation to provide natural decompression of the structures of the carpal tunnel. Significant expansion of the carpal tunnel is thereby achieved to relieve pressure on the median nerve and to relieve the pain, inflamation and irritation of the surrounding tissues. A tensioning means is also provided for holding the proximal bones of the wrist in a fixed spaced relationship allowing the flexor retinaculum to relax thereby relieving the pressure on the median nerve and remediating the effects of carpal tunnel syndrome.

The functions of the present invention are accomplished without wrapping or supporting the wrist and without significant restrictions on hand or wrist motion.

BRIEF DESCRIPTION OF THE DRAWINGS

For the purpose of illustrating the invention, there is shown in the drawings forms which are presently preferred; it being understood, however, that the invention is not limited to the precise arrangements and instrumentalities shown.

FIG. 1 is an isometric view of a human hand showing the narrowing of the carpal tunnel and the pinching of the median nerve.

FIG. 2 is an isometric view of a normal carpal tunnel.

DETAILED DESCRIPTION OF THE INVENTION

Figure 8:
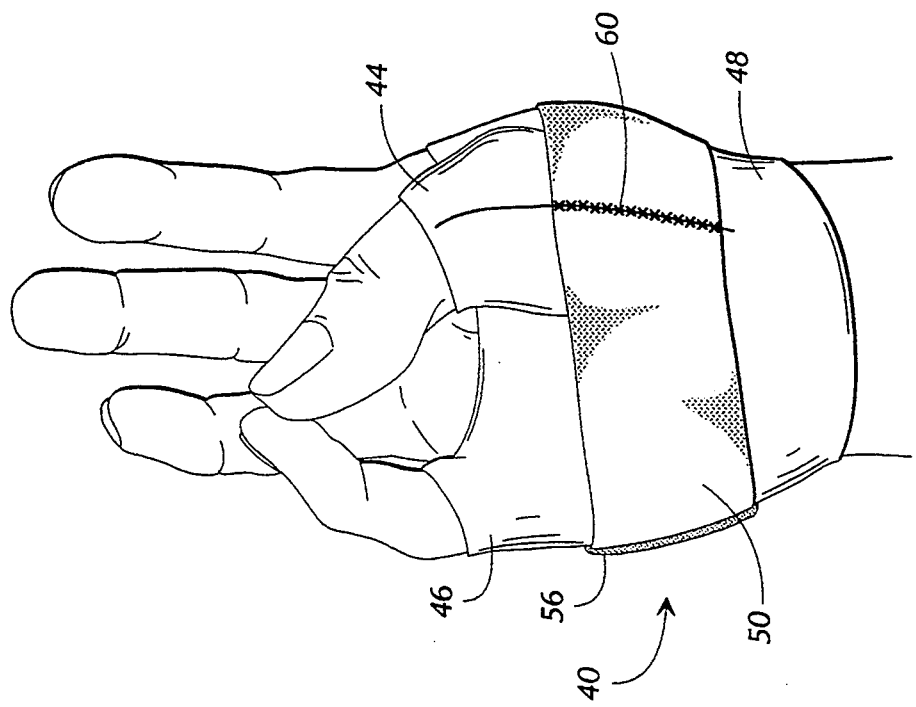
FIG. 8 is a palmar view of the remedial prophylaxis or carpal tunnel mitt of the present invention disposed over a human hand in the "pinch" position.

The following detailed description is of the best presently contemplated mode of carrying out the invention. The description is not intended in a limiting sense, and is made solely for the purpose of illustrating the general principles of the invention. The various features and advantages of the present invention may be more readily understood with reference to the following detailed description taken in conjunction with the accompanying drawings.

Referring now to the drawings in detail, where like numerals refer to like parts or elements, there is shown in FIG. 1 a human hand 10 having a normal configuration. Within the lower wrist and proximal area of the hand a ligamentous band connects the borders of the carpal bones creating the carpal tunnel 12. Housed within the carpal tunnel 12 are the various carpal bones;

the pisiform 14, the triquetrum 16, the lunate 18, and the scaphoid 20. Bridging the top of the carpal tunnel 12 is the transverse carpal ligament, the flexor retinaculum 22. Also within the carpal tunnel 12 are various tendons 24 for manipulating the various phalanges (or fingers) and the median nerve 26 which provides motor and sensory signals to and from the hand. In FIG. 1 the median nerve 26 is shown in a compressed state as the carpal tunnel 12 has narrowed due to repeated bending of the wrist causing inflammation and swelling of the tissues. The swelling of the bursae and tendons causes a reduction or narrowing of the carpal tunnel 12 compressing or pinching the median nerve 26 resulting in tingling, numbness and pain in the first two fingers and thumb of the hand 10, generally represented as the area indicated by the dot 28. The tingling, numbness and pain may extend to the other fingers of the hand 10. In both cases pain may possibly extend up the arm to the elbow or shoulder. Strength of the thumb may be impaired if the condition continues without treatment.

Figure 3:
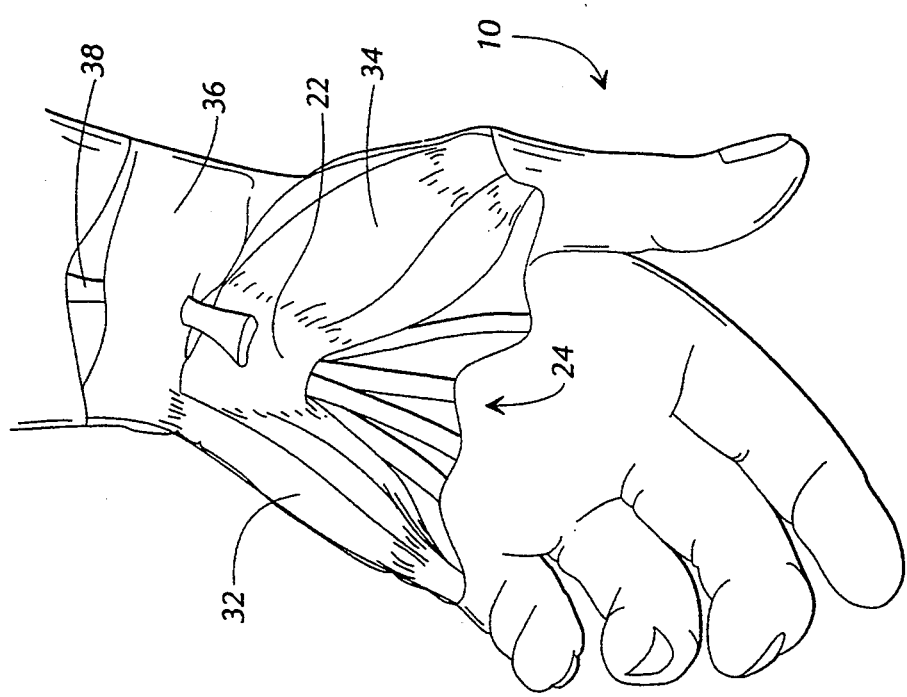
FIG. 3 is an isometric view of the ligament structure of the human hand surrounding the carpal tunnel.

Referring now to FIG. 3, the various ligaments and muscles which surround the carpal tunnel 12 are shown. The transverse carpal ligament 22 lies directly over the various tendons 24 for controlling the phalanges. To the left is the hypothenar muscle group 32 and to the right is the thenar muscle group 34. Proximal to the transverse carpal ligament 22 is the volar carpal ligament 36 which lies over the palmarus longus tendon 38. Repetitive strain abuse of the tendons and bursue under a tensioned transverse carpal ligament identified in FIGS. 1 and 3 will result in the symptoms called carpal tunnel syndrome.

In comparison to the trauma of carpal tunnel syndrome represented in FIG. 1, one can compare the normal arrangement of the tissues in FIG. 2 and readily see the tendons 24 are not swollen and the median nerve is not compressed. With the onset of carpal tunnel syndrome it is the express purpose of the present invention to remediate the trauma without the need for invasive surgery, and without the need for motion restrictive applicances as heretofore required.

Figure 5:
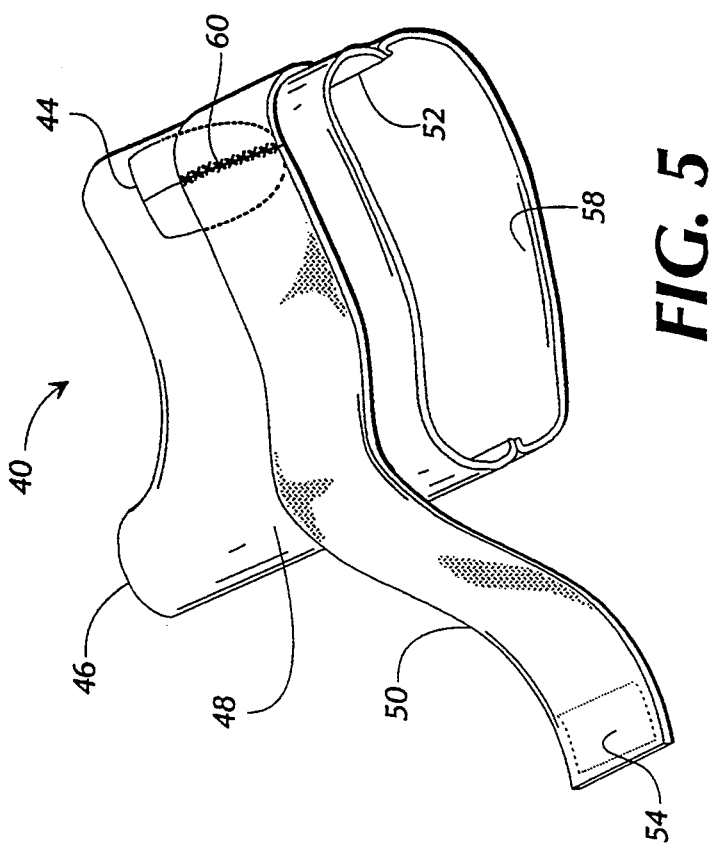
FIG. 5 is an isometric (palmar) view of the remedial prophylaxis or carpal tunnel mitt of the present invention.
Figure 4:
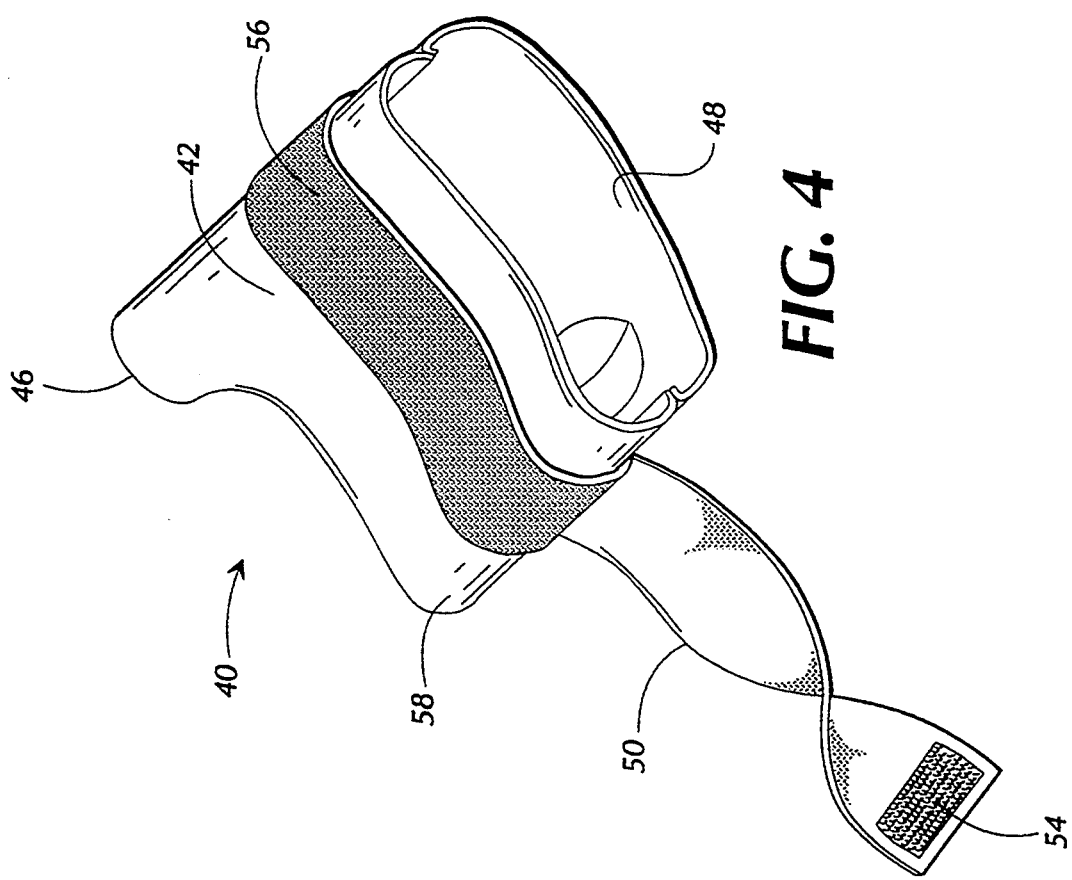
FIG. 4 is an isometric (dorsal) view of the remedial prophylaxis or carpal tunnel mitt of the present invention.

With reference to FIGS. 4 and 5, the remedial prophylaxis or carpal tunnel mitt is shown generally as 40. The palmar view (FIG. 5) of the carpal tunnel mitt 40 shows a glove-like member 42 for fitting over the hand with "finger holes" for the thumb and fourth finger, 44, 46, respectively, with a single large cutout for the other three fingers lying between. The palmar element 48 of the glove-like member 42 is preferred to be manufactured of an elasticized material to conform to the particular surfaces of the hand which material should be porous to permit the underlying skin to breathe as well as lightweight for ease of wear. The thumb sleeve or hole 44 is preferred to be of the same material and may either be stitched to the member 42 or formed as a part thereof.

The tensioning means 50 circumscribes the glove-like member 42 being anchored into the lateral seam at 52. The tensioning means 50 is of sufficient length to wrap around the member 42 and hand almost entirely with a hook-type fastening means 54 located on the inner surface of the distal or free end of the tensioning means 50 for fastening to a fabric patch 56 on the dorsal element 58 of the member 42.

The dorsal element 58 of the glove-like member 42 is assembled to the palmar element 48 by stitching or other similar attachment technique and is preferred to be manufactured of a non-elastic material of sufficient suppleness to comfortably conform to the back of the hand, but exhibiting a resistance to elastic deformation. The fabric patch 56 for fastening adjustable attachment of the elastic band 50 lies across the dorsal element 58 and is sewn or similarly attached at the seams joining the palmar and dorsal elements 48, 58.

Figure 7:
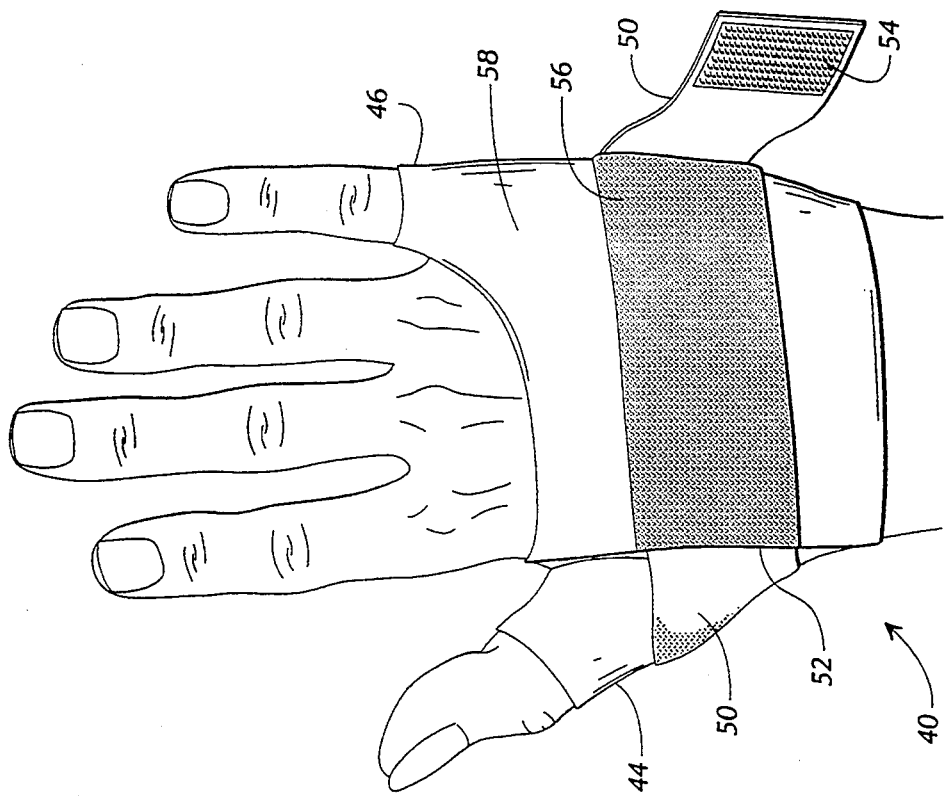
FIG. 7 is a dorsal view of the remedial prophylaxis or carpal tunnel mitt of the present invention disposed over a human hand.
Figure 6:
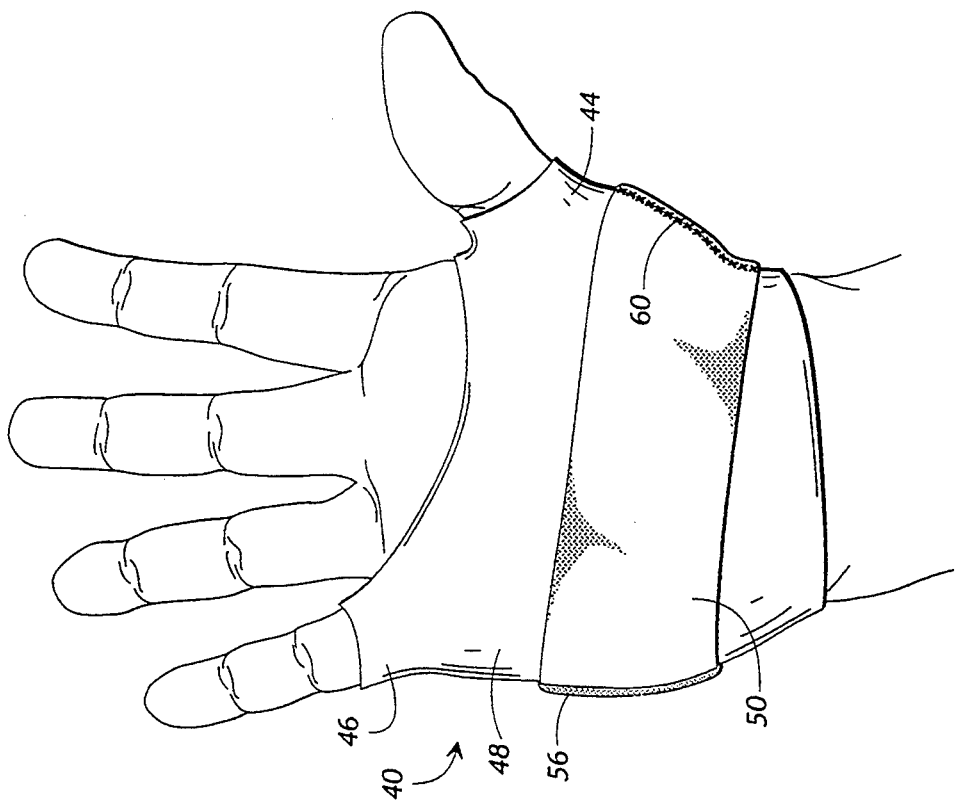
FIG. 6 is a palmar view of the remedial prophylaxis or carpal tunnel mitt of the present invention disposed over a human hand.

Returning to the thumb sleeve 44, the elastic band 50 is anchored to the sleeve 44 by "x stitching" 60 at a predetermined angular relationship to the seam joining the palmar and dorsal elements 48, 58. The angular displacement of the tensioning means 50 is desired to bisect the mid-metacarpal region of the first and fifth digits of the hand. The termination point of the tensioning means 50 is to be at the same angular displacement on the dorsal side of the hand. The anchoring of the elastic band 50 to the thumb sleeve 44 on the palmar element 48 and the placement of the fabric patch 56 on the dorsal element 58 creates the desired orientation of the band 50 across the palmar portion and around to the dorsal side of the hand. The "x stitching" 60 orients the elastic band 50 so that the band crosses the palm of the hand in a direct line to overly the mid-portion of the opposite side and restricts the slipping of the band upwards or downwards from the proper position. A loop of fabric may be substituted for the "x-stitching" 60 and serve as an alternate means for properly positioning the elastic band 50 so that, as the band 50 traverses across the palm of the hand, the band will lie in a direct line to the preferred location on the heel of the hand; the mid-portion of the heel, as shown in FIGS. 6, 7 and 8. This arrangement of elements can be readily observed by reference to FIG. 6 showing the glove-like member 42 with a relaxed elastic band 50 crossing the palm of the hand, traversing the heel, and attaching to the fabric patch 56 without any tensioning force across the palmar portion of the hand.

FIG. 7 provides the reverse view of that shown in FIG. 6 showing the carpal tunnel mitt 40 disposed over the hand with the elastic band 50 extending away from the heel of the hand, and not attached to the patch 56 on the dorsal element 58. Again, there is no tensioning force exerted across the palmar region of the hand as in FIG. 6.

Referring to FIG. 8, the hand is shown in a "pinch" position as a tensioning force is exerted across the palmar portion of the hand by the elastic band 50. The tensioning force places the first (thumb) and fifth phalanges in opposition effecting an immediate reduction in the stretch of the transverse carpal ligament 22 and the deepening of the carpal tunnel 12 relieving the compression force on the median nerve 26. As the tensioning force is effected across the palmar region of the hand the elastic characteristic of the palmar member 48 conforms the member to the contours of the palm to reduce or minimize any pressure points due to fabric creases and eliminate the possible trapping of objects on the palmar surface of the carpal tunnel mitt 40. All of this is accomplished without significantly reducing the manual dexterity of the hand wearing the carpal tunnel mitt 40.

The "pinch" position of the hand in FIG. 8 wearing the carpal tunnel mitt 40 with the tensioning force applied by the elastic band or tensioning means 50 demonstrates the physical mechanism of elastic approximation of the first and fifth carpal-metacarpal regions for deepening of the carpal tunnel 12 to achieve as close an approximation of structure and orientation of tissues of a normal carpal tunnel as shown in FIG. 2 and the immediate reduction of the stretch of the transverse carpal ligament 22. This is accomplished by physically bringing the pisiform and scaphoid bones (14, 20) closer together by altering slightly the curvature of the carpal bones through the inward compression of the palmar region of the hand against the transverse carpal ligament 22 by exerting the tensioning force across the palmar region. It is extremely important to retain the elastic band 50 at, or as close as possible to, the median of the heel of the hand and to prevent migration upward or downward of the band. This provides the optimal conditions for support for the carpal tunnel 12 and the transverse carpal ligament 22, which is the desired remediation to alleviate carpal tunnel syndrome while wearing the carpal tunnel mitt 40.

Application of the carpal tunnel mitt 40 can be appreciated from the various drawings as the mitt 40 is applied as one would pull on a glove. The first phalange (thumb) slides comfortably into the elasticized thumb sleeve 44 and the fifth phalange slides into the hole 46 provided for it. The remaining digits are unencumbered by either the apparatus or excess material which could reduce air circulation to the skin. Once the carpal tunnel mitt 40 is pulled entirely on over the phalanges, the elastic band 50 is drawn across the palmar region, creating a tensioning force, and fastened to the fabric patch 56 via the hook-type fastening means 54. Removal is accomplished by reversing the steps set out above.

The spirit of this invention is captured in the unique approach to management of the mechanism which contribute to the production of carpal tunnel syndrome. The remedial prophylaxis or carpal tunnel mitt 40 may be utilized in conjunction with other remedial devices such as the Sebastian or Aziz splinting devices used for the immobilization of the lower arm or wrist region of the body. The carpal tunnel mitt 40 may be applied to the hand beneath either of these splinting devices for assistance in the non-invasive healing process.

The present invention may be embodied in other specific forms without departing from the spirit or essential attributes thereof, and, accordingly, reference should be made to the appended claims, rather than to the specification, as indicating the scope of the invention.

We claim:

1. Apparatus for remedial prophylaxis of carpal tunnel syndrome comprising a flexible, lightweight glove means having a dorsal side, a palmar side, and a lateral seam for placement over and in proximate contact with a hand, said glove having first and second finger hole means for receiving the fourth finger and thumb, said first and second finger hole means adapted to extend at least partially along the fourth finger and thumb; a single cutout extending between said first and second finger hole means and adapted for receiving the first, second and third fingers; and a tensioning means anchored to said lateral seam of the glove means proximate to the finger hole means which receives the thumb for wrapping over the palmar side of the glove means and securing to the dorsal side of the glove means for holding the first and fifth metacarpal regions of the hand in fixed opposition to each other to provide decompression of the structures of the carpal tunnel.

2. The apparatus of claim 1 further comprising a tensioning means positioning means adjacent the finger hole means which receives the thumb for orienting the tensioning means properly across the palmar side of the hand and around to the dorsal side of the hand.

3. The apparatus of claim 2 wherein the positioning means for the tensioning means is a loop through which the tensioning means passes for aligning the tensioning means to pass over the mid-portion of the heel of the hand.

4. The apparatus of claim 2 wherein the positioning means for the tensioning means is a series of stitchings securing the tensioning means to the finger hole means which receives the thumb for aligning the tensioning means to pass over the mid-portion of the heel of the hand.

5. The apparatus of claim 1 wherein the glove means is comprised of a palmar member made of an elastic material and a dorsal member made of a non-elastic material.

6. The apparatus of claim 5 wherein the elastic material conforms to the particular surfaces of the palmar portion of the hand when the glove means is subjected to the compression of the tensioning means across the palmar portion of the hand for reducing pressure due to fabric creases.

7. The apparatus of claim 5 wherein the non-elastic material is of sufficient suppleness to conform to the dorsal portion of the hand while exhibiting resistance to elastic deformation.

8. The apparatus of claim 1 wherein the force applied to the hand by the tensioning means effects a reducing of the stretch of the transverse carpal ligament and the deepening of the carpal tunnel for relieving the compression force on the median nerve without reducing the manual dexterity of the hand.

9. The apparatus of claim 1 wherein the tensioning means are infinitely adjustable for providing the selected degree of decompression to the structures of the carpal tunnel.

10. The apparatus of claim 1 wherein the glove means are usable in conjunction with other hand wrappings and arm splinting means to effect a reducing of the stretch of the transverse carpal ligament and the deepening of the carpal tunnel for relieving the compression force on the median nerve without reducing the manual dexterity of the hand.

11. A method of remedial prophylaxis of carpal tunnel syndrome through decompression of the structures of the carpal tunnel by effecting a reduction of the stretch of the transverse carpal ligament and the deepening of the carpal tunnel for relieving the compression force on the median nerve without reducing the manual dexterity of the hand comprising the steps of:

providing a flexible lightweight glove means having a dorsal side, a palmar side, and a lateral seam for placement over and in proximate contact with a hand, said glove means having first and second finger hole means for receiving the fourth finger and thumb, said first and second finger hole means adapted to extend at least partially along the fourth finger and thumb, and a single cutout extending between said first and second finger hole means and adapted for receiving the first, second and third fingers;

providing a tensioning means anchored to said lateral seam of the glove means proximate to the finger hole means which receives the thumb for wrapping over the palmar side of the glove means and securing to the dorsal side of the glove means for holding the first and fifth metacarpal regions of the hand in fixed opposition to each other; and providing positioning means for orienting the tensioning means properly across the palmar side of the hand and around to the dorsal side of the hand.

12. The method in accordance with claim 11 further comprising the step of providing an infinitely adjustable tensioning means to apply the selected degree of decompression to the structures of the carpal tunnel.

* * * * *